United States Patent
Closson et al.

(10) Patent No.: US 9,850,191 B2
(45) Date of Patent: Dec. 26, 2017

(54) ALDEHYDE COMPOUNDS AND THEIR USE IN PERFUME COMPOSITIONS

(71) Applicant: INTERNATIONAL FLAVORS & FRAGRANCES INC, New York, NY (US)

(72) Inventors: Adam P. Closson, Hoboken, NJ (US); Ryan Oesterle, Jackson, NJ (US); Anthony T. Levorse, Jr., Westfield, NJ (US); Anubhav P. S. Narula, Hazlet, NJ (US); Michael G. Monteleone, Hazlet, NJ (US)

(73) Assignee: INTERNATIONAL FLAVORS & FRAGRANCES INC., New York, NY (US)

(*) Notice: Subject to any disclaimer, the term of this patent is extended or adjusted under 35 U.S.C. 154(b) by 0 days.

(21) Appl. No.: 15/068,172

(22) Filed: Mar. 11, 2016

(65) Prior Publication Data
US 2016/0281027 A1 Sep. 29, 2016

Related U.S. Application Data

(60) Provisional application No. 62/139,154, filed on Mar. 27, 2015.

(51) Int. Cl.
| | |
|---|---|
| *C11B 9/00* | (2006.01) |
| *C11D 3/50* | (2006.01) |
| *C11D 3/20* | (2006.01) |
| *A61K 8/33* | (2006.01) |
| *A61Q 5/00* | (2006.01) |
| *A61Q 15/00* | (2006.01) |
| *A61Q 11/00* | (2006.01) |
| *A61Q 19/00* | (2006.01) |
| *C07C 43/164* | (2006.01) |
| *C07D 309/20* | (2006.01) |
| *A61K 8/49* | (2006.01) |
| *A61Q 13/00* | (2006.01) |
| *C07D 309/18* | (2006.01) |
| *C07C 43/166* | (2006.01) |

(52) U.S. Cl.
CPC .............. *C07C 43/164* (2013.01); *A61K 8/33* (2013.01); *A61K 8/498* (2013.01); *A61Q 5/00* (2013.01); *A61Q 11/00* (2013.01); *A61Q 13/00* (2013.01); *A61Q 15/00* (2013.01); *A61Q 19/00* (2013.01); *C07C 43/166* (2013.01); *C07D 309/18* (2013.01); *C07D 309/20* (2013.01); *C11B 9/008* (2013.01); *C11B 9/0015* (2013.01); *C11B 9/0061* (2013.01); *C11D 3/2068* (2013.01); *C11D 3/2072* (2013.01); *C11D 3/50* (2013.01); *A61K 2800/10* (2013.01)

(58) Field of Classification Search
None
See application file for complete search history.

(56) References Cited

U.S. PATENT DOCUMENTS 5,116,813 A * 5/1992 Tajima .................. C07C 31/125
512/25

FOREIGN PATENT DOCUMENTS

| GB | 981702 | 1/1965 | |
|---|---|---|---|
| GB | 1025045 | 4/1966 | |
| GB | 1025046 | 4/1966 | |
| GB | 1025047 | 4/1966 | |
| GB | 1025047 A * | 4/1966 | ............. C07C 45/62 |

OTHER PUBLICATIONS

V. Jarolim and F. Sorm, "Preparation of Some Acyclic Juvenoidal Analogues", Collection Czechoslov. Chem. Commun., vol. 41, (pp. 1066-1072) (1976).

* cited by examiner

*Primary Examiner* — Frederick Krass
*Assistant Examiner* — Michael P Cohen
(74) *Attorney, Agent, or Firm* — Martin Zhang; XuFan Tseng; Elizabeth M Stover

(57) ABSTRACT

The present invention is directed to novel aldehyde compounds and a method of improving, enhancing or modifying a fragrance formulation through the addition of an olfactory acceptable amount of the novel aldehyde compounds.

4 Claims, No Drawings

ALDEHYDE COMPOUNDS AND THEIR USE IN PERFUME COMPOSITIONS

STATUS OF RELATED APPLICATIONS

This application claims priority to U.S. Provisional Patent Application No. 62/139,154, filed Mar. 27, 2015, the contents hereby incorporated by reference as if set forth in its entirety.

FIELD OF THE INVENTION

The present invention relates to new chemical entities and their use as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allow the perfumers to apply the new compounds in creating new fragrances.

SUMMARY OF THE INVENTION

The present invention provides novel aldehyde compounds and their unexpected advantageous use in enhancing, improving or modifying the fragrance of perfumes, colognes, toilet water, fabric care products, personal products and the like.

One embodiment of the present invention relates to novel aldehyde compounds represented by Formula I set forth below:

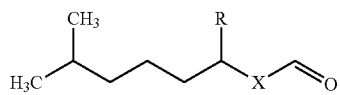

Formula I wherein R represents a methyl or an ethyl group; and X represents an alkylene group containing 3 or 4 carbon atoms, with the proviso that the total number of carbon atoms in the compound is 13.

Another embodiment of the present invention relates to a novel aldehyde compound selected from the group consisting of 5-ethyl-9-methyl-decanal, 4-ethyl-2,8-dimethyl-nonanal and 6,10-dimethyl-undecanal.

Another embodiment of the present invention relates to a fragrance composition comprising the aldehyde compounds provided above.

Another embodiment of the present invention relates to a fragrance product comprising the aldehyde compounds provided above.

Another embodiment of the present invention relates to a method of improving, enhancing or modifying a fragrance formulation through the addition of an olfactory acceptable amount of the aldehyde compounds provided above.

These and other embodiments of the present invention will be apparent by reading the following specification.

DETAILED DESCRIPTION OF THE INVENTION

The novel aldehyde compounds represented by Formula I of the present invention are represented by following examples.

5-Ethyl-9-methyl-decanal

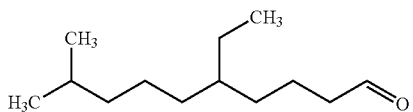

4-Ethyl-2,8-dimethyl-nonanal

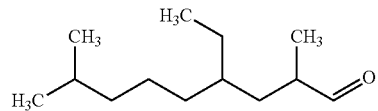

6,10-Dimethyl-undecanal

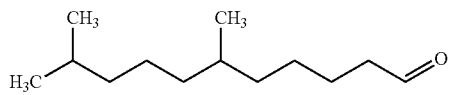

2,5,9-Trimethyl-decanal

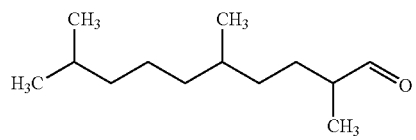

Those with skill in the art will recognize that the compounds of the present invention may have a number of isomers such as positional or optical isomers. It is intended herein that the compounds described herein include isomeric mixtures as well as single isomers that may be separated using techniques known to those having skill in the art. Suitable techniques include chromatography such as high performance liquid chromatography, referred to as HPLC, and particularly silica gel chromatography and gas chromatography trapping known as GC trapping. Yet, commercial products are mostly offered as isomeric mixtures.

The preparation of the compounds of the present invention is detailed in the Examples. Materials were purchased from Aldrich Chemical Company unless noted otherwise.

The use of the compounds of the present invention is widely applicable in current perfumery products, including the preparation of perfumes and colognes, the perfuming of personal care products such as soaps, shower gels, and hair care products, fabric care products, air fresheners, and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art. Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The compounds of the present invention can be used in combination with a complementary fragrance compound. The term "complementary fragrance compound" as used herein is defined as a fragrance compound selected from the group consisting of 2-[(4-methylphenyl)methylene]-heptanal (Acalea), iso-amyl oxyacetic acid allylester (Allyl Amyl Glycolate), (3,3-dimethylcyclohexyl)ethyl ethyl propane-1,3-dioate (Applelide), (E/Z)-1-ethoxy-1-decene (Arctical), 2-ethyl-4-(2,2,3-trimethyl-3-cyclo-penten-1-yl)-2-buten-1-ol (Bacdanol), 2-methyl-3-[(1,7,7-trimethylbicyclo[2.2.1]hept-2-yl)oxy]exo-1-propanol (Bornafix), 1,2,3,5,6,7-hexahydro-1,1,2,3,3-pentamethyl-4H-inden-4-one (Cashmeran), trimethylcyclopentenylmethyloxabicyclooctane (Cassiffix), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano-1H-inden-5/6-yl acetate (Cyclacet), 3A,4,5,6,7,7A-hexahydro-4,7-methano-1H-inden-5/6-yl propinoate (Cyclaprop), 3A,4,5,6,7,7A-hexahydro-4,7-methano-1G-inden-5/6-yl butyrate (Cyclobutanate), 1-(2,6,6-trimethyl-3-cyclohexen-1-yl)-2-buten-1-one (Delta Damascone), 3-(4-ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4,6,7,8-hexahydro-4,6,6,7,8,8-hexamethylcyclopenta-gamma-2-benzopyran (Galaxolide), 1-(5,5-dimethyl-1-cyclohexen-1-yl)pent-4-en-1-one (Galbascone), E/Z-3,7-dimethyl-2,6-octadien-1-yl acetate (Geranyl Acetate), α-methyl-1,3-benzodioxole-5-propanal (Helional), 1-(2,6,6-trimethyl-2-cyclohexen-1-yl)-1,6-heptadien-3-one (Hexalon), (Z)-3-hexenyl-2-hydroxybenzoate (Hexenyl Salicylate, CIS-3), 4-(2,6,6-trimethyl-2-cyclohexen-1-yl)-3-buten-2-one (Ionone a), 1-(1,2,3,4,5,6,7,8-octahydro-2,3,8,8-tetramethyl-2-naphthalenyl)-ethan-1-one (Iso E Super), methyl 3-oxo-2-pentylcyclopentaneacetate (Kharismal), 2,2,4-trimethyl-4-phenyl-butanenitrile (Khusinil), 3,4,5,6,6-pentamethylhept-3-en-2-one (Koavone), 3/4-(4-hydroxy-4-methyl-pentyl) cyclohexene-1-carboxaldehyde (Lyral), 3-methyl-4-(2,6,6-trimethyl-2-cyclohexen-1-yl)-3-buten-2-one (Methyl Ionone y), 1-(2,6,6-trimethyl-2-cyclohexen-1-yl) pent-1-en-3-one (Methyl Ionone a Extra, Methyl Ionone N), 3-methyl-4-phenylbutan-2-ol (Muguesia), cyclopentadec-4-en-1-one (Musk Z4), 3,3,4,5,5-pentamethyl-11,13-dioxatricyclo[7.4.0.0<2,6>]tridec-2(6)-ene (Nebulone), 3,7-dimethyl-2,6-octadien-1-yl acetate (Neryl Acetate), 3,7-dimethyl-1,3,6-octatriene (Ocimene), ortho-tolylethanol (Peomosa), 3-methyl-5-phenylpentanol (Phenoxanol), 1-methyl-4-(4-methyl-3-pentenyl)cyclohex-3-ene-1-carboxaldehyde (Precyclemone B), 4-methyl-8-methylene-2-adamantanol (Prismantol), 2-ethyl-4-(2,2,3-trimethyl-3-cyclopenten-1-yl)-2-buten-1-ol (Sanjinol), 2-methyl-4-(2,2,3-trimethyl-3-cyclopenten-1-yl)-2-buten-1-ol (Santaliff), Terpineol, 2,4-dimethyl-3-cyclohexene-1-carboxaldehyde (Triplal), decahydro-2,6,6,7,8,8-hexamethyl-2H-indeno[4,5-B]furan (Trisamber), 2-tert-butylcyclohexyl acetate (Verdox), 4-tert-butylcyclohexyL acetate (Vertenex), acetyl cedrene (Vertofix), 3,6/4,6-dimethylcyclohex-3-ene-1-carboxaldehyde (Vertoliff), and (3Z)-1-[(2-methyl-2-propenyl)oxy]-3-hexene (Vivaldie).

The term "alkyl" means a linear or branched saturated monovalent hydrocarbon, e.g., methyl, ethyl, propyl, 2-propyl, butyl (including all isomeric forms), pentyl (including all isomeric forms), hexyl (including all isomeric forms), and the like. The term "alkenyl" means a linear or branched unsaturated, aliphatic hydrocarbon containing at least one carbon-carbon double bond. The term "alkylene" refers to bivalent alkyl. Examples include —$CH_2$—, —$CH_2CH_2$—, —$CH_2CH_2CH_2$—, —$CH_2(CH_3)CH_2$—, —$CH_2CH_2CH_2CH_2$—, and the like.

The terms "fragrance formulation", "fragrance composition", and "perfume composition" mean the same and refer to a consumer composition that is a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance formulation of the present invention is a consumer composition comprising a compound of the present invention. The fragrance formulation of the present invention comprises a compound of the present invention and further a complementary fragrance compound as defined above.

The term "fragrance product" means a consumer product containing a fragrance ingredient that adds fragrance or masks malodor. Fragrance products may include, for example, perfumes, colognes, bar soaps, liquid soaps, shower gels, foam baths, cosmetics, skin care products such as creams, lotions and shaving products, hair care products for shampooing, rinsing, conditioning, bleaching, coloring, dyeing and styling, deodorants and antiperspirants, feminine care products such as tampons and feminine napkins, baby care products such as diapers, bibs and wipes, family care products such as bath tissues, facial tissues, paper handkerchiefs or paper towels, fabric products such as fabric softeners and fresheners, air care products such as air fresheners and fragrance delivery systems, cosmetic preparations, cleaning agents and disinfectants such as detergents, dishwashing materials, scrubbing compositions, glass and metal cleaners such as window cleaners, countertop cleaners, floor and carpet cleaners, toilet cleaners and bleach additives, washing agents such as all-purpose, heavy duty, and hand washing or fine fabric washing agents including laundry detergents and rinse additives, dental and oral hygiene products such as toothpastes, tooth gels, dental flosses, denture cleansers, denture adhesives, dentifrices, tooth whitening and mouthwashes, health care and nutritional products and food products such as snack and beverage products. The fragrance product of the present invention is a consumer product that contains a compound of the present invention. The fragrance product of the present invention contains a compound of the present invention and further a complementary fragrance compound as defined above.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character. The term "modifying" is understood to mean providing the fragrance formulation with a change in character.

The term "olfactory acceptable amount" is understood to mean the amount of a compound in a fragrance formulation, wherein the compound will contribute its individual olfactory characteristics. However, the olfactory effect of the fragrance formulation will be the sum of effect of each of the fragrance ingredients. Thus, the compound of the present invention can be used to improve or enhance the aroma characteristics of the fragrance formulation, or by modifying the olfactory reaction contributed by other ingredients in the formulation. The olfactory acceptable amount may vary depending on many factors including other ingredients, their relative amounts and the olfactory effect that is desired.

The amount of the compounds of the present invention employed in a fragrance formulation varies from about 0.005 to about 70 weight percent, preferably from 0.005 to about 50 weight percent, more preferably from about 0.5 to about 25 weight percent, and even more preferably from about 1 to about 10 weight percent. Those with skill in the art will be able to employ the desired amount to provide desired fragrance effect and intensity. In addition to the compounds of the present invention, other materials can also be used in conjunction with the fragrance formulation to encapsulate and/or deliver the fragrance. Some well-known materials are, for example, but not limited to, polymers, oligomers, other non-polymers such as surfactants, emulsifiers, lipids including fats, waxes and phospholipids, organic oils, mineral oils, petrolatum, natural oils, perfume fixatives, fibers, starches, sugars and solid surface materials such as zeolite and silica.

When used in a fragrance formulation these ingredients provide additional notes to make a fragrance formulation more desirable and noticeable, and add the perception of value. The odor qualities found in these materials assist in beautifying and enhancing the finished accord as well as improving the performance of the other materials in the fragrance.

In addition, the compounds of the present invention are also surprisingly found to provide superior ingredient performance and possess unexpected advantages in malodor counteracting applications such as body perspiration, environmental odor such as mold and mildew, bathroom, and etc. The compounds of the present invention substantially eliminate the perception of malodors and/or prevent the formation of such malodors, thus, can be utilized with a vast number of functional products.

Examples of the functional products are provided herein to illustrate the various aspects of the present invention. However, they do not intend to limit the scope of the present invention. The functional products may include, for example, a conventional room freshener (or deodorant) composition such as room freshener sprays, an aerosol or other spray, fragrance diffusers, a wick or other liquid system, or a solid, for instance candles or a wax base as in pomanders and plastics, powders as in sachets or dry sprays or gels, as in solid gel sticks, clothes deodorants as applied by washing machine applications such as in detergents, powders, liquids, whiteners or fabric softeners, fabric refreshers, linen sprays, closet blocks, closet aerosol sprays, or clothes storage areas or in dry cleaning to overcome residual solvent notes on clothes, bathroom accessories such as paper towels, bathroom tissues, sanitary napkins, towellets, disposable wash cloths, disposable diapers, and diaper pail deodorants, cleansers such as disinfectants and toilet bowl cleaners, cosmetic products such as antiperspirant and deodorants, general body deodorants in the form of powders, aerosols, liquids or solid, or hair care products such as hair sprays, conditioners, rinses, hair colors and dyes, permanent waves, depilatories, hair straighteners, hair groom applications such as pomade, creams and lotions, medicated hair care products containing such ingredients as selenium sulphide, coal tar or salicylates, or shampoos, or foot care products such as foot powders, liquids or colognes, after shaves and body lotions, or soaps and synthetic detergents such as bars, liquids, foams or powders, odor control such as during manufacturing processes, such as in the textile finishing industry and the printing industry (inks and paper), effluent control such as in processes involved in pulping, stock yard and meat processings, sewage treatment, garbage bags, or garbage disposal, or in product odor control as in textile finished goods, rubber finished goods or car fresheners, agricultural and pet care products such as dog and hen house effluents and domestic animal and pet care products such as deodorants, shampoo or cleaning agents, or animal litter material and in large scale closed air systems such as auditoria, and subways and transport systems.

Thus, it will be seen that the composition of the invention is usually one in which the malodor counteractant is present together with a carrier by means of which or from which the malodor counteractant can be introduced into air space wherein the malodor is present, or a substrate on which the malodor has deposited. For example, the carrier can be an aerosol propellant such as a chlorofluoro-methane, or a solid such as a wax, plastics material, rubber, inert powder or gel. In a wick-type air freshener, the carrier is a substantially odorless liquid of low volatility. In several applications, a composition of the invention contains a surface active agent or a disinfectant, while in others, the malodor counteractant is present on a fibrous substrate. In many compositions of the invention there is also present a fragrance component which imparts a fragrance to the composition. The fragrances stated above can all be employed.

Malodor counteracting effective amount is understood to mean the amount of the inventive malodor counteractant employed in a functional product that is organoleptically effective to abate a given malodor while reducing the combined intensity of the odor level, wherein the given malodor is present in air space or has deposited on a substrate. The exact amount of malodor counteractant agent employed may vary depending upon the type of malodor counteractant, the type of the carrier employed, and the level of malodor counteractancy desired. In general, the amount of malodor counteractant agent present is the ordinary dosage required to obtain the desired result. Such dosage is known to the skilled practitioner in the art. In a preferred embodiment, when used in conjunction with malodorous solid or liquid functional products, e.g., soap and detergent, the compounds of the present invention may be present in an amount ranging from about 0.005 to about 50 weight percent, preferably from about 0.01 to about 20 weight percent, and more preferably from about 0.05 to about 5 weight percent, and when used in conjunction with malodorous gaseous functional products, the compounds of the present invention may be present in an amount ranging from about 0.1 to 10 mg per cubic meter of air.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, L is understood to be liter, mL is understood to be milliliter, g is understood to be gram, Kg is understood to be kilogram, mol is understood to be mole, psi is understood to be pound-force per square inch, and mmHg be millimeters (mm) of mercury (Hg). IFF as used in the examples is understood to mean International Flavors & Fragrances Inc., New York, N.Y., USA.

Example I

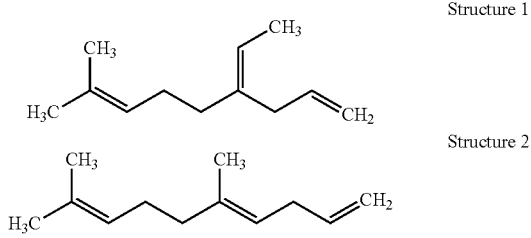

Preparation of 4-Ethylidene-8-methyl-nona-1,7-diene (Structure 1) and 5,9-Dimethyl-deca-1,4,8-triene (Structure 2)

A 3-L round bottom flask purged with nitrogen was charged with cobalt bromide (CoBr$_2$) (91 g, 0.42 mol), 1,2,-bis(diphenylphosphino)ethane (Ph$_2$P(CH$_2$)$_2$PPh$_2$) (167 g, 0.42 mol) and zinc iodide (ZnI$_2$) (41 g, 0.63 mol). The resulting mixture was dissolved in degassed methylene chloride (CH$_2$Cl$_2$) (2.0 L). Myrcene ((CH$_3$)$_2$CCH(CH$_2$)$_2$C(CH$_2$)(CHCH$_2$)) (585 g, 4.2 mol) was added followed by tetrabutylammonium borohydride ((CH$_3$CH$_2$CH$_2$CH$_2$)$_4$N(BH$_4$)) (152 g, 0.63 mol). Ethylene gas was then bubbled through the reaction at room temperature. The reaction mixture was aged for 48 hours and then filtered through a silica plug. The solvent was removed in vacuo. The remaining residue was distilled through a column packed with ceramic saddles to afford a mixture of 4-ethylidene-8-methyl-nona-1,7-diene (Structure 1) and 5,9-Dimethyl-deca-1,4,8-triene (Structure 2) in a 4:1 ratio (600 g, 3.6 mol).

4-Ethylidene-8-methyl-nona-1,7-diene has the following NMR spectral characteristics:
$^1$H NMR (500 MHz, CDCl$_3$): 5.71-5.86 (m, 1H), 5.32 (m, 1H), 4.94-5.20 (m, 3H), 2.80 (d, J=6.4 Hz, 2H), 1.97-2.13 (m, 4H), 1.69 (s, 3H), 1.58-1.64 (m, 6H).

5,9-Dimethyl-deca-1,4,8-triene has the following NMR spectral characteristics:
$^1$H NMR (500 MHz, CDCl$_3$): 5.71-5.86 (m, 1H), 5.32 (m, 1H), 4.94-5.20 (m, 3H), 2.76 (dd, J=6.4, 6.2 Hz, 2H), 1.97-2.13 (m, 4H), 1.58-1.72 (m, 9H).

Example II

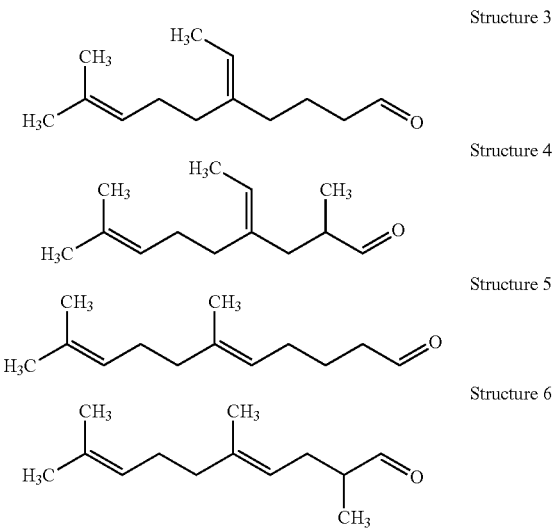

Preparation of 5-Ethylidene-9-methyl-dec-8-enal (Structure 3), 4-Ethylidene-2,8-dimethyl-non-7-enal (Structure 4), 6,10-Dimethyl-undeca-5,9-dienal (Structure 5) and 2,5,9-Trimethyl-deca-4,8-dienal (Structure 6)

The mixture of 4-ethylidene-8-methyl-nona-1,7-diene and 5,9-dimethyl-deca-1,4,8-triene (prepared above in EXAMPLE I) (275 g, 1.67 mol) was subjected to pressurized syngas in the presence of tris(triphenylphosphine)rhodium hydridocarbonyl. The reaction mixture was heated to 100° C. for 6 hours and then cooled to room temperature. The resulting mixture was distilled under reduced pressure to afford a mixture of 5-ethylidene-9-methyl-dec-8-enal (Structure 3), 4-ethylidene-2,8-dimethyl-non-7-enal (Structure 4), 6,10-dimethyl-undeca-5,9-dienal (Structure 5) and 2,5,9-trimethyl-deca-4,8-dienal (Structure 6) in a 64:15:11:5 ratio (150 g, 0.77 mol).

5-Ethylidene-9-methyl-dec-8-enal has the following NMR spectral characteristics:
$^1$H NMR (500 MHz, CDCl$_3$): 9.77 (t, J=1.7 Hz, 1H), 5.28 (q, J=6.6 Hz, 1H), 5.09 (t, J=6.8 Hz, 1H), 2.41 (td, J=7.3, 1.7 Hz, 2H), 1.96-2.12 (m, 6H), 1.65-1.77 (m, 2H), 1.68 (s, 3H), 1.60 (s, 3H), 1.58 (d, J=7.1 Hz, 3H).

4-Ethylidene-2,8-dimethyl-non-7-enal has the following NMR spectral characteristics:
$^1$H NMR (500 MHz, CDCl$_3$): 9.65 (d, J=1.8 Hz, 1H), 5.28 (q, J=6.6 Hz, 1H), 5.09 (t, J=6.8 Hz, 1H), 2.44-2.57 (m, 1H), 1.88-2.20 (m, 6H), 1.68 (s, 3H), 1.60 (s, 3H), 1.58 (d, J=7.1 Hz, 3H), 1.06 (d, J=7.0 Hz, 3H).

6,10-Dimethyl-undeca-5,9-dienal has the following NMR spectral characteristics:
$^1$H NMR (500 MHz, CDCl$_3$): 9.77 (t, J=1.7 Hz, 1H), 5.06-5.15 (m, 2H), 2.41 (td, J=7.3, 1.7 Hz, 2H), 1.88-2.20 (m, 8H), 1.56-1.63 (m, 9H).

2,5,9-Trimethyl-deca-4,8-dienal has the following NMR spectral characteristics:
$^1$H NMR (500 MHz, CDCl$_3$): 9.65 (d, J=1.8 Hz, 1H), 5.06-5.15 (m, 2H), 2.44-2.57 (m, 1H), 1.88-2.20 (m, 6H), 1.56-1.63 (m, 9H), 1.06 (d, J=7.0 Hz, 3H).

The mixture of 5-ethylidene-9-methyl-dec-8-enal, 4-ethylidene-2,8-dimethyl-non-7-enal, 6,10-dimethyl-undeca-5,9-dienal and 2,5,9-trimethyl-deca-4,8-dienal was described as having strong floral, spicy, green, citrus, muguet and ozonic notes but with metallic and rubbery characters.

Example III

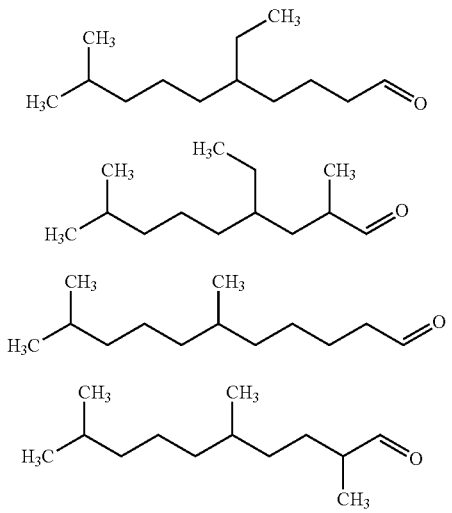

Structure 7

Structure 8

Structure 9

Structure 10

Preparation of 5-Ethyl-9-methyl-decanal (Structure 7), 4-Ethyl-2,8-dimethyl-nonanal (Structure 8), 6,10-Dimethyl-undecanal (Structure 9) and 2,5,9-Trimethyl-decanal (Structure 10)

The mixture of 5-ethylidene-9-methyl-dec-8-enal, 4-ethylidene-2,8-dimethyl-non-7-enal, 6,10-dimethyl-undeca-5,9-dienal and 2,5,9-trimethyl-deca-4,8-dienal (prepared above in EXAMPLE II) (136 g, 0.70 mol) was subjected to pressurized hydrogen in the presence of palladium on carbon and heated to 60° C. for 6 hours. The resulting mixture was filtered and fractionally distilled to afford a mixture of 5-ethyl-9-methyl-decanal (Structure 7), 4-ethyl-2,8-dimethyl-nonanal (Structure 8), 6,10-dimethyl-undecanal (Structure 9) and 2,5,9-trimethyl-decanal (Structure 10) in a 64:15:11:5 ratio (111 g, 0.56 mol).

5-Ethyl-9-methyl-decanal has the following NMR spectral characteristics:
$^1$H NMR (400 MHz, CDCl$_3$): 9.77 (t, J=1.8 Hz, 1H), 2.41 (td, J=7.3, 1.8 Hz, 2H), 1.47-1.66 (m, 3H), 1.10-1.34 (m, 11H), 0.87 (d, J=6.7 Hz, 6H), 0.84 (t, J=7.3 Hz, 3H).

4-Ethyl-2,8-dimethyl-nonanal has the following NMR spectral characteristics:
$^1$H NMR (400 MHz, CDCl$_3$): 9.57 (t, J=1.9 Hz, 1H), 2.50 (td, J=7.2, 1.9 Hz, 2H), 1.47-1.70 (m, 3H), 1.10-1.32 (m, 11H), 0.86 (d, J=6.7 Hz, 6H), 0.87 (t, J=7.2 Hz, 3H).

6,10-Dimethyl-undecanal has the following NMR spectral characteristics:
$^1$H NMR (400 MHz, CDCl$_3$): 9.75 (t, J=1.8 Hz, 1H), 2.42 (td, J=7.1, 1.8 Hz, 2H), 1.40-1.58 (m, 3H), 1.04-1.28 (m, 11H), 0.86 (d, J=6.5 Hz, 6H), 0.84 (t, J=7.2 Hz, 3H).

2,5,9-Trimethyl-decanal has the following NMR spectral characteristics:
$^1$H NMR (400 MHz, CDCl$_3$): 9.57 (t, J=1.7 Hz, 1H), 2.36 (td, J=7.1, 1.7 Hz, 2H), 1.40-1.52 (m, 3H), 1.05-1.30 (m, 11H), 0.86 (d, J=6.5 Hz, 6H), 0.85 (t, J=7.1 Hz, 3H).

The mixture of 5-ethyl-9-methyl-decanal, 4-ethyl-2,8-dimethyl-nonanal, 6,10-dimethyl-undecanal and 2,5,9-trimethyl-decanal was described as having strong woody, spicy, citrus and sweet notes.

Example IV

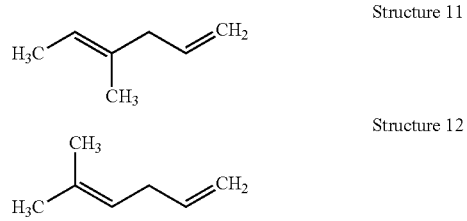

Structure 11

Structure 12

Preparation of 4-Methyl-hexa-1,4-diene (Structure 11) and 5-Methyl-hexa-1,4-diene (Structure 12)

4-Methyl-hexa-1,4-diene (Structure 11) and 5-methyl-hexa-1,4-diene (Structure 12) were prepared similarly according to EXAMPLE I using isoprene (375 g, 5.5 mol). The mixture of 4-methyl-hexa-1,4-diene and 5-methyl-hexa-1,4-diene in a 5:4 ratio was obtained (401 g, 4.18 mol).

4-Methyl-hexa-1,4-diene has the following NMR spectral characteristics:
$^1$H NMR (500 MHz, CDCl$_3$): 5.78-5.83 (m, 1H), 5.29 (q, J=7.3 Hz, 1H), 4.93-5.06 (m, 2H), 2.73-2.75 (m, 2H), 1.67 (s, 3H), 1.58 (d, J=6.6 Hz, 3H).

5-Methyl-hexa-1,4-diene has the following NMR spectral characteristics:
$^1$H NMR (500 MHz, CDCl$_3$): 5.71-5.83 (m, 1H), 5.15 (q, J=7.3 Hz, 1H), 4.93-5.06 (m, 2H), 2.77 (d, J=6.6 Hz, 2H), 1.72 (s, 3H), 1.62 (s, 3H).

Example V

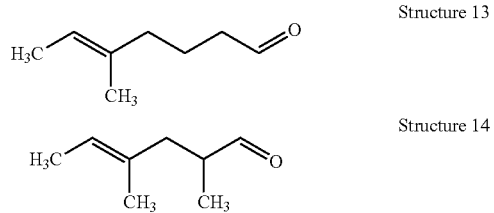

Structure 13

Structure 14

Preparation of 5-Methyl-hept-5-enal (Structure 13) and 2,4-Dimethyl-hex-4-enal (Structure 14)

5-Methyl-hept-5-enal (Structure 13) and 2,4-dimethyl-hex-4-enal (Structure 14) were prepared similarly according to EXAMPLE II using the mixture of 4-methyl-hexa-1,4-diene and 5-methyl-hexa-1,4-diene (prepared above in BIV) (404 g, 4.2 mol). The mixture of 5-methyl-hept-5-enal and 2,4-dimethyl-hex-4-enal in a 4:1 ratio was obtained (228 g, 1.8 mol).

5-Methyl-hept-5-enal has the following NMR spectral characteristics:
$^1$H NMR (400 MHz, CDCl$_3$): 9.77 (t, J=1.8 Hz, 1H), 5.26 (q, J=6.8 Hz, 1H), 2.41 (td, J=7.3, 1.8 Hz, 2H), 2.08 (d, J=7.6 Hz, 2H), 1.66-1.78 (m, 2H), 1.64 (br s, 3H), 1.55 (d, J=6.8 Hz, 3H).

2,4-Dimethyl-hex-4-enal has the following NMR spectral characteristics:
$^1$H NMR (500 MHz, CDCl$_3$): 9.66 (d, J=1.84 Hz, 1H), 5.36 (q, J=6.8 Hz, 1H), 2.04-2.58 (m, 3H), 1.69 (br s, 3H), 1.58 (d, J=6.8 Hz, 3H), 1.06 (d, J=7.0 Hz, 3H).

The mixture of 5-methyl-hept-5-enal and 2,4-dimethyl-hex-4-enal was described as having green and ozonic but with metallic, rubbery and fishy characters.

Example VI

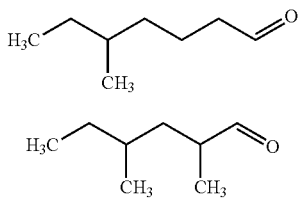

Structure 15

Structure 16

Preparation of 5-Methyl-heptanal (Structure 15) and 2,4-Dimethy-hexanal (Structure 16)

5-Methyl-heptanal (Structure 15) and 2,4-dimethy-hexanal (Structure 16) were prepared similarly according to EXAMPLE III using the mixture of 5-methyl-hept-5-enal and 2,4 dimethyl-hex-4-enal (prepared above in EXAMPLE V) (150 g, 1.10 mol). The mixture of 5-methyl-heptanal and 2,4-dimethy-hexanal in a 4:1 ratio was obtained (72 g, 0.56 mol).

5-Methyl-heptanal has the following NMR spectral characteristics:
$^1$H NMR (400 MHz, CDCl$_3$): 9.71 (t, J=1.7 Hz, 1H), 2.31-2.40 (m, 2H), 1.48-1.66 (m, 2H), 1.22-1.34 (m, 3H), 1.05-1.17 (m, 2H), 0.77-0.86 (m, 6H).

2,4-Dimethy-hexanal has the following NMR spectral characteristics:
$^1$H NMR (400 MHz, CDCl$_3$): 9.52-9.57 (m, 1H), 2.30-2.41 (m, 1H), 1.05-1.72 (m, 5H), 1.01 (d, J=6.0 Hz, 3H), 0.77-0.86 (m, 6H).

The mixture of 5-methyl-heptanal and 2,4-dimethy-hexanal was described as having floral, green and fruity notes but with an ozonic character and solventy perception.

Example VII

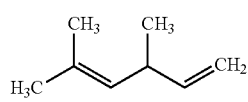

Structure 17

Preparation of 3,5-Dimethyl-hexa-1,4-diene (Structure 17)

3,5-Dimethyl-hexa-1,4-diene (Structure 17) was prepared similarly according to EXAMPLE I using methylpentadiene ((CH$_3$)$_2$CCHCHCH$_2$) (500 g, 6.0 mol). 3,5-Dimethyl-hexa-1,4-diene (365 g, 3.3 mol) was obtained.
$^1$H NMR (500 MHz, CDCl$_3$): 5.75 (ddd, J=17.0, 10.4, 6.2 Hz, 1H), 4.85-5.01 (m, 3H), 2.99-3.10 (m, 1H), 1.70 (d, J=1.3 Hz, 3H), 1.62 (d, J=1.4 Hz, 3H), 1.03 (d, J=6.9 Hz, 3H).

Example VIII

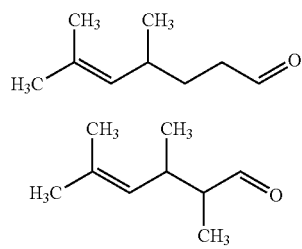

Structure 18

Structure 19

Preparation of 4,6-Dimethyl-hept-5-enal (Structure 18) and 2,3,5-Trimethyl-hex-4-enal (Structure 19)

4,6-Dimethyl-hept-5-enal (Structure 18) and 2,3,5-trimethyl-hex-4-enal (Structure 19) were prepared similarly according to EXAMPLE II using 3,5-dimethyl-hexa-1,4-diene (prepared above in EXAMPLE VII) (911 g, 8.2 mol). The mixture of 4,6-dimethyl-hept-5-enal and 2,3,5-trimethyl-hex-4-enal in a 4:1 ratio was obtained (817 g, 5.8 mol).

4,6-Dimethyl-hept-5-enal has the following NMR spectral characteristics:
$^1$H NMR (400 MHz, CDCl$_3$): 9.73 (t, J=1.8 Hz, 1H), 4.83 (br d, J=9.5 Hz, 1H), 2.30-2.43 (m, 3H), 1.68 (s, 3H), 1.59 (s, 3H), 1.40-1.73 (m, 2H), 0.93-1.06 (m, 3H).

2,3,5-Trimethyl-hex-4-enal has the following NMR spectral characteristics:
$^1$H NMR (400 MHz, CDCl$_3$): 9.62 (d, J=2.8 Hz, 1H), 5.02 (br d, J=9.8 Hz, 1H), 2.63-2.82 (m, 1H), 2.17-2.27 (m, 1H), 1.70 (s, 3H), 1.64 (s, 3H), 0.93-1.06 (m, 6H).

The mixture of 4,6-dimethyl-hept-5-enal and 2,3,5-trimethyl-hex-4-enal was described as having floral, green, vegetal and chemical notes.

Example IX

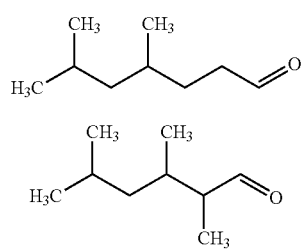

Structure 20

Structure 21

Preparation of 4,6-Dimethyl-heptanal (Structure 20) and 2,3,5-Trimethyl-hexanal (Structure 21)

4,6-Dimethyl-heptanal (Structure 20) and 2,3,5-trimethyl-hexanal (Structure 21) were prepared similarly according to EXAMPLE III using 4,6-dimethyl-hept-5-enal and 2,3,5-trimethyl-hex-4-enal (prepared above in EXAMPLE VIII) (94 g, 0.67 mol). The mixture of 4,6-dimethyl-heptanal and 2,3,5-trimethyl-hexanal in a 4:1 ratio was obtained (48 g, 0.33 mol).

4,6-Dimethyl-heptanal has the following NMR spectral characteristics:

$^1$H NMR (400 MHz, CDCl$_3$): 9.77 (t, J=1.8 Hz, 1H), 2.36-2.50 (m, 2H), 1.35-1.72 (m, 4H), 0.81-1.23 (m, 9H).

2,3,5-Trimethyl-hexanal has the following NMR spectral characteristics:

$^1$H NMR (400 MHz, CDCl$_3$): 9.65-9.69 (m, 1H), 2.21-2.33 (m, 1H), 1.35-1.72 (m, 4H), 0.81-1.23 (m, 10H).

The mixture of 4,6-dimethyl-heptanal and 2,3,5-trimethyl-hexanal was described as having floral, spicy and green notes but with a solvently character.

Example X

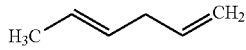

Structure 22

Preparation of Hexa-1,4-diene (Structure 22)

Hexa-1,4-diene was prepared similarly according to EXAMPLE I using butadiene (CH$_2$(CH)$_2$CH$_2$) (300 g, 5.5 mol) with ethylene gas. Hexa-1,4-diene (315 g, 3.8 mol) was obtained.

$^1$H NMR (400 MHz, CDCl$_3$): 5.81 (m, 1H), 5.38-5.58 (m, 2H), 4.95-5.07 (m, 2H), 2.77-2.83 (m, 2H), 1.62 (m, 3H).

Example XI

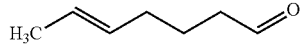

Structure 23

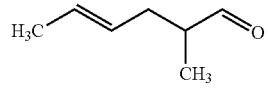

Structue 24

Preparation of Hept-5-enal (Structure 23) and 2-Methyl-hex-4-enal (Structure 24)

Hept-5-enal (Structure 23) and 2-methyl-hex-4-enal (Structure 24) were prepared similarly according to EXAMPLE II using hexa-1,4-diene (prepared above in EXAMPLE X) (615 g, 7.4 mol). The mixture of hept-5-enal and 2-methyl-hex-4-enal in a 4:1 ratio was obtained (660 g, 5.8 mol).

Hept-5-enal has the following NMR spectral characteristics:

$^1$H NMR (400 MHz, CDCl$_3$): 9.77 (t, J=1.6 Hz, 1H), 5.29-5.62 (m, 2H), 2.37-2.49 (m, 2H), 2.02-2.21 (m, 2H), 1.66-1.75 (m, 2H), 1.60 (d, J=6.7 Hz, 3H).

2-Methyl-hex-4-enal has the following NMR spectral characteristics:

$^1$H NMR (400 MHz, CDCl$_3$): 9.66 (t, J=1.0 Hz, 1H), 5.29-5.62 (m, 2H), 2.14-2.47 (m, 3H), 1.62 (d, J=7.0 Hz, 3H), 1.11 (d, J=6.8 Hz, 3H).

The mixture of hept-5-enal and 2-methyl-hex-4-enal was described as having floral and green notes but with gassy and oily characters.

Example XII

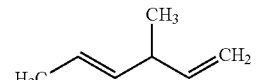

Structure 25

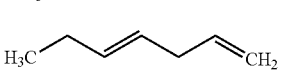

Structure 26

Preparation of 3-Methyl-hexa-1,4-diene (Structure 25) and Hepta-1,4-diene (Structure 26)

3-Methyl-hexa-1,4-diene (Structure 25) and hepta-1,4-diene (Structure 26) were prepared similarly according to EXAMPLE I using piperylene (CH$_2$(CH)$_3$CH$_3$) (244 g, 3.5 mol) with ethylene gas. The mixture of 3-methyl-hexa-1,4-diene and hepta-1,4-diene in a 8:1 ratio was obtained (100 g, 1.0 mol).

3-Methyl-hexa-1,4-diene has the following NMR spectral characteristics:

$^1$H NMR (400 MHz, CDCl$_3$): 5.72-5.83 (m, 1H), 5.39-5.49 (m, 1H), 5.19-5.27 (m, 1H), 4.88-5.01 (m, 2H), 3.13-3.24 (m, 1H), 1.63 (dd, J=6.8, 1.8 Hz, 3H), 1.06 (d, J=6.8 Hz, 3H).

Hepta-1,4-diene has the following NMR spectral characteristics:

$^1$H NMR (400 MHz, CDCl$_3$): 5.72-5.86 (m, 1H), 5.30-5.49 (m, 2H), 4.93-5.05 (m, 2H), 2.75-2.82 (m, 2H), 1.99-2.11 (m, 2H), 0.96 (t, J=7.5 Hz, 3H).

Example XIII

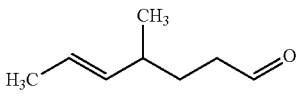

Structure 27

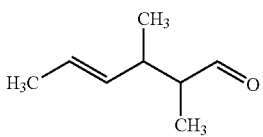

Structure 28

Preparation of 4-Methyl-hept-5-enal (Structure 27) and 2,3-Dimethyl-hex-4-enal (Structure 28)

4-Methyl-hept-5-enal (Structure 27) and 2,3-dimethyl-hex-4-enal (Structure 28) were prepared similarly according to EXAMPLE II using the mixture of 3-methyl-hexa-1,4-diene and hepta-1,4-diene (prepared above in EXAMPLE XII) (957 g, 9.9 mol). The mixture of 4-methyl-hept-5-enal and 2,3-dimethyl-hex-4-enal in a 7:3 ratio was obtained (848 g, 6.7 mol).

4-Methyl-hept-5-enal has the following NMR spectral characteristics:

$^{1}$H NMR (400 MHz, CDCl$_{3}$): 9.75 (t, J=1.8 Hz, 1H), 5.05-5.55 (m, 2H), 2.45-2.56 (m, 1H), 2.22-2.45 (m, 2H), 1.43-1.74 (m, 2H), 1.59 (dd, J=6.9, 1.8 Hz, 3H), 0.98 (d, J=6.7 Hz, 3H).

2,3-Dimethyl-hex-4-enal has the following NMR spectral characteristics:

$^{1}$H NMR (400 MHz, CDCl$_{3}$): 9.64 (d, J=2.5 Hz, 1H), 5.05-5.55 (m, 2H), 2.75-2.95 (m, 1H), 2.17-2.32 (m, 1H), 1.64 (dd, J=6.9, 1.8 Hz, 3H), 0.99-1.10 (m, 6H).

The mixture of 4-methyl-hept-5-enal and 2,3-dimethyl-hex-4-enal was described as having green, fruity and ozonic notes but with fatty and chemical characters.

Example XIV

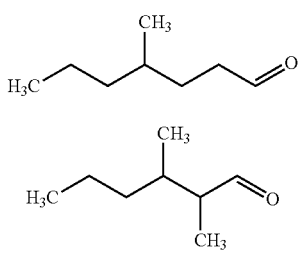

Structure 29

Structure 30

Preparation of 4-Methyl-heptanal (Structure 29) and 2,3-Dimethyl-hexanal (Structure 30)

4-Methyl-heptanal (Structure 29) and 2,3-dimethyl-hexanal (Structure 30) were prepared similarly according to EXAMPLE III using the mixture of 4-methyl-hept-5-enal and 2,3-dimethyl-hex-4-enal (prepared above in EXAMPLE XIII) (100 g, 0.79 mol). The mixture of 4-methyl-heptanal and 2,3-dimethyl-hexanal in a 7:3 ratio was obtained (76 g, 0.59 mol).

4-Methyl-heptanal has the following NMR spectral characteristics:

$^{1}$H NMR (400 MHz, CDCl$_{3}$): 9.74-9.79 (m, 1H), 2.37-2.50 (m, 2H), 0.79-1.74 (m, 13H).

2,3-Dimethyl-hexanal has the following NMR spectral characteristics:

$^{1}$H NMR (400 MHz, CDCl$_{3}$): 9.64-9.69 (m, 1H), 2.23-2.39 (m, 1H), 0.79-1.74 (m, 14H).

The mixture of 4-methyl-heptanal and 2,3-dimethyl-hexanal was described as having green and chemical notes with additional fatty and rubbery characters.

Example XV

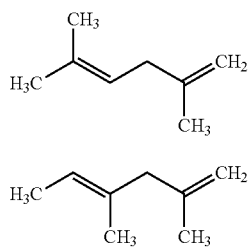

Structure 31

Structure 32

Preparation of 2,5-Dimethyl-hexa-1,4-diene (Structure 31) and 2,4-Dimethyl-hexa-1,4-diene (Structure 32)

2,5-Dimethyl-hexa-1,4-diene (Structure 31) and 2,4-dimethyl-hexa-1,4-diene (Structure 32) were prepared similarly according to EXAMPLE I using isoprene (CH$_{2}$C(CH$_{3}$)CHCH$_{2}$) (400 g, 5.8 mol) with propylene gas. The mixture of 2,5-dimethyl-hexa-1,4-diene and 2,4-dimethyl-hexa-1,4-diene in a 3:1 ratio was obtained (264 g, 2.4 mol).

2,5-Dimethyl-hexa-1,4-diene has the following NMR spectral characteristics:

$^{1}$H NMR (400 MHz, CDCl$_{3}$): 5.14-5.20 (m, 1H), 4.65-4.75 (m, 2H), 2.64-2.74 (m, 2H), 1.56-1.75 (m, 9H).

2,4-Dimethyl-hexa-1,4-diene has the following NMR spectral characteristics:

$^{1}$H NMR (400 MHz, CDCl$_{3}$): 5.30-5.37 (m, 1H), 4.65-4.75 (m, 2H), 2.64-2.74 (m, 2H), 1.56-1.75 (m, 9H).

Example XVI

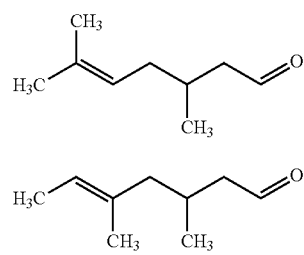

Structure 33

Structure 34

Preparation of 3,6-Dimethyl-hept-5-enal (Structure 33) and 3,5-Dimethyl-hept-5-enal (Structure 34)

3,6-Dimethyl-hept-5-enal (Structure 33) and 3,5-dimethyl-hept-5-enal (Structure 34) were prepared similarly according to EXAMPLE II using the mixture of 2,5-dimethyl-hexa-1,4-diene and 2,4-dimethyl-hexa-1,4-diene (prepared above in EXAMPLE XV) (957 g, 9.9 mol). The mixture of 3,6-dimethyl-hept-5-enal and 3,5-dimethyl-hept-5-enal in a 4:1 ratio was obtained (753 g, 5.3 mol).

3,6-Dimethyl-hept-5-enal has the following NMR spectral characteristics:

$^{1}$H NMR (400 MHz, CDCl$_{3}$): 9.74 (t, J=2.3 Hz, 1H), 5.06-5.16 (m, 1H), 1.90-2.34 (m, 5H), 1.70 (s, 3H), 1.59 (s, 3H), 0.97 (d, J=6.6 Hz, 3H).

3,5-Dimethyl-hept-5-enal has the following NMR spectral characteristics:

$^{1}$H NMR (400 MHz, CDCl$_{3}$): 9.74 (t, J=2.3 Hz, 1H), 5.27-5.36 (m, 1H), 2.34-2.46 (m, 1H), 1.91-2.25 (m, 4H), 1.66-1.70 (m, 3H), 1.54-1.62 (m, 3H), 0.96 (d, J=6.5 Hz, 3H).

The mixture of 3,6-dimethyl-hept-5-enal and 3,5-dimethyl-hept-5-enal was described as having woody, floral, green, citrus, fruity and ozonic notes but with plastic character.

Example XVII

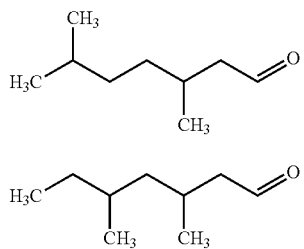

Structure 35

Structure 36

Preparation of 3,6-Dimethyl-heptanal (Structure 35) and 3,5-Dimethyl-heptanal (Structure 36)

3,6-Dimethyl-heptanal (Structure 35) and 3,5-dimethyl-heptanal (Structure 36) were prepared similarly according to EXAMPLE III using the mixture of 3,6-dimethyl-hept-5-enal and 3,5-dimethyl-hept-5-enal (prepared above in EXAMPLE XVI) (97 g, 0.69 mol). The mixture of 3,6-dimethyl-heptanal and 3,5-dimethyl-heptanal in a 4:1 ratio was obtained (46 g, 0.32 mol).

3,6-Dimethyl-heptanal has the following NMR spectral characteristics:

$^1$H NMR (400 MHz, CDCl$_3$): 9.76 (t, J=2.3 Hz, 1H), 2.35-2.45 (m, 1H), 2.17-2.28 (m, 1H), 1.92-2.10 (m, 1H), 1.43-1.58 (m, 1H), 1.12-1.40 (m, 4H), 0.96 (d, J=6.7 Hz, 3H), 0.84-0.91 (m, 6H).

3,5-Dimethyl-heptanal has the following NMR spectral characteristics:

$^1$H NMR (400 MHz, CDCl$_3$): 9.76 (t, J=2.3 Hz, 1H), 2.28-2.10 (m, 3H), 1.30 (m, 5H), 0.9 (d, 3H, J=6.6 Hz), 0.84 (d, 3H, J=6.5 Hz), 0.83 (d, 3H, J=7.2 Hz).

The mixture of 3,6-dimethyl-heptanal and 3,5-dimethyl-heptanal was described as having floral, spicy, green, citrus and sweaty notes.

Example XVIII

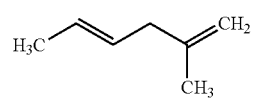

Structure 37

Preparation of 2-Methyl-hexa-1,4-diene (Structure 37)

2-Methyl-hexa-1,4-diene was prepared similarly according to EXAMPLE I using butadiene (300 g, 5.5 mol) with propylene gas. 2-Methyl-hexa-1,4-diene (279 g, 2.8 mol) was obtained.

$^1$H NMR (400 MHz, CDCl$_3$): 5.51-5.60 (m, 1H), 5.39-5.49 (m, 1H), 4.68-4.74 (m, 2H), 2.74 (d, J=7.3 Hz, 2H), 1.73 (s, 3H), 1.58-1.66 (m, 3H)

Example XIX

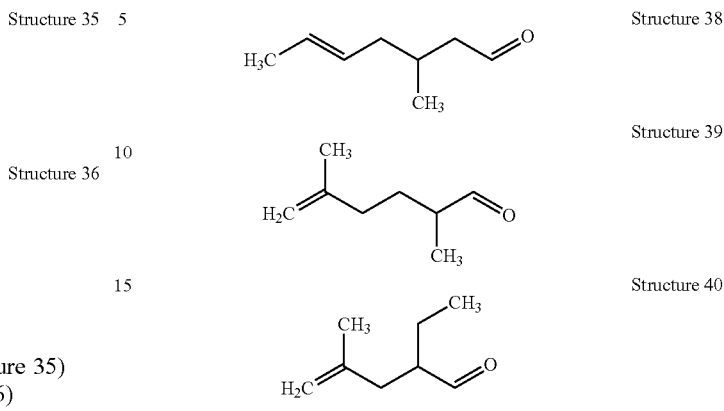

Structure 38

Structure 39

Structure 40

Preparation of 3-Methyl-hept-5-enal (Structure 38), 2,5-Dimethyl-hex-5-enal (Structure 39) and 2-Ethyl-4-methyl-pent-4-enal (Structure 40)

3-Methyl-hept-5-enal (Structure 38), 2,5-dimethyl-hex-5-enal (Structure 39) and 2-ethyl-4-methyl-pent-4-enal (Structure 40) were prepared similarly according to EXAMPLE II using 2-methyl-hexa-1,4-diene (prepared above in EXAMPLE XVIII) (539 g, 5.6 mol). The mixture of 3-methyl-hept-5-enal, 2,5-dimethyl-hex-5-enal and 2-ethyl-4-methyl-pent-4-enal in a 4:3:2 ratio was obtained (298 g, 2.3 mol).

3-Methyl-hept-5-enal has the following NMR spectral characteristics:

$^1$H NMR (400 MHz, CDCl$_3$): 9.76 (t, J=2.2 Hz, 1H), 5.30-5.61 (m, 2H), 1.43-2.48 (m, 5H), 1.60 (d, J=6.8 Hz, 3H), 1.12 (d, J=7.0 Hz, 3H).

2,5-Dimethyl-hex-5-enal has the following NMR spectral characteristics:

$^1$H NMR (400 MHz, CDCl$_3$): 9.64 (d, J=1.9 Hz, 1H), 4.65-4.83 (m, 2H), 1.43-2.48 (m, 5H), 1.73 (s, 3H), 0.98 (d, J=6.5 Hz, 3H).

2-Ethyl-4-methyl-pent-4-enal has the following NMR spectral characteristics:

$^1$H NMR (400 MHz, CDCl$_3$): 9.58 (d, J=2.6 Hz, 1H), 4.65-4.83 (m, 2H), 1.43-2.48 (m, 5H), 1.73 (s, 3H), 0.93 (t, J=7.5 Hz, 3H).

The mixture of 3-methyl-hept-5-enal, 2,5-dimethyl-hex-5-enal and 2-ethyl-4-methyl-pent-4-enal was described as having spicy, aldehydic, green and woody notes but with cuminic character.

Example XX

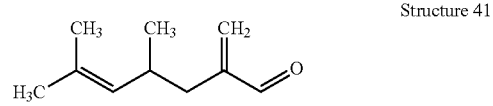

Structure 41

Preparation of 4,6-Dimethyl-2-methylene-hept-5-enal (Structure 41)

A 3-L round bottom flask fitted with an overhead stirrer was charged with di-n-butylamine (($CH_3(CH_2)_3)_2NH$) (8.2 g, 0.064 mol), acetic acid (3.8 g, 0.064 mol) and formaldehyde solution (35%, 118 g, 1.3 mol) and then heated to 50° C. The mixture of 4,6-dimethyl-hept-5-enal and 2,3,5-trimethyl-hex-4-enal (prepared above in EXAMPLE VIII) (149 g, 1.06 mol) was fed in. When gas-liquid chromatography (GLC) analysis indicated the completion of the reaction, the reaction mixture was cooled to room temperature and toluene was added. The resulting layers were shaken in a separatory funnel and separated. The aqueous layer was further extracted with toluene and the organic layers were combined, washed with brine solution followed by sodium carbonate solution. Simple distillation of the resulting mixture afforded 4,6-dimethyl-2-methylene-hept-5-enal (115 g, 0.75 mol).

Example XXI

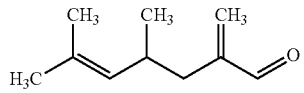

Structure 42

Preparation of 2,4,6-Trimethyl-hept-5-enal (Structure 42)

4,6-Dimethyl-2-methylene-hept-5-enal (prepared above in EXAMPLE XX) (116 g, 0.76 mol) was subjected to pressurized hydrogen in the presence of palladium on carbon and heated to 60° C. for 6 hours. The resulting mixture was filtered and fractionally distilled to afford 2,4,6-trimethyl-hept-5-enal was obtained (82 g, 0.53 mol).

$^1$H NMR (400 MHz, CDCl$_3$): 9.59 (d, J=1.8 Hz, 50% of 1H), 9.56 (d, J=1.8 Hz, 50% of 1H), 4.76-4.91 (m, 1H), 2.22-2.55 (m, 2H), 1.61-1.76 (m, 1H), 1.67 (s, 3H), 1.60 (s, 50% of 3H), 1.57 (s, 50% of 3H), 1.19-1.30 (m, 1H), 1.03-1.09 (m, 3H), 0.96 (d, J=6.5 Hz, 50% of 3H), 0.93 (d, J=6.7 Hz, 50% of 3H).

2,4,6-Trimethyl-hept-5-enal was described as having floral, aldehydic and green but weak notes.

Example XXII

In addition, following aldehydes were obtained and their fragrance properties were evaluated, respectively.

Decanal (commercially available at Taytonn Pte Ltd):

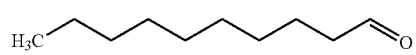

Structure 43

Decanal was described as having citrus, crispy and clean but simple notes.

Dodecanal (commercially available at Kao Corporation):

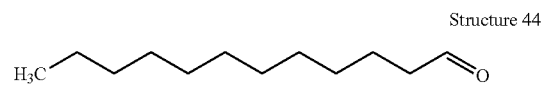

Structure 44

Dodecanal was described as having strong but chemical notes.

Tetradecanal (commercially available at Givaudan S.A.):

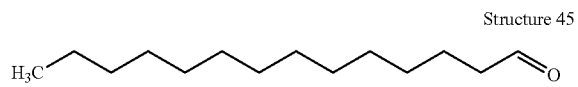

Structure 45

Tetradecanal was described as having strong but chemical and fatty notes.

5,9-Dimethyl-decanal was prepared according to the above examples.

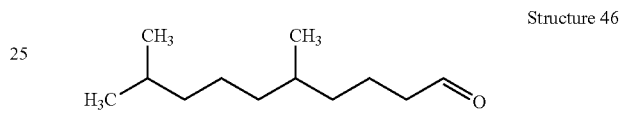

Structure 46

$^1$H NMR (400 MHz, CDCl$_3$): 9.78 (t, J=1.8 Hz, 1H), 2.42 (dt, J=7.4, 1.8 Hz, 2H), 0.98-1.79 (m, 12H), 0.88 (d, J=6.7 Hz, 6H), 0.88 (d, J=6.7 Hz, 3H).

5,9-Dimethyl-decanal was described as having spicy and aldehydic but weak and simple notes.

Example XXIII

The fragrance properties of the above compounds are reported in the following:

| Structure No. | Compound | Odor Profile |
| --- | --- | --- |
| Mixture of Structure 3, 4, 5 and 6 | 5-Ethylidene-9-methyl-dec-8-enal, 4-ethylidene-2,8-dimethyl-non-7-enal, 6,10-dimethyl-undeca-5,9-dienal and 2,5,9-trimethyl-deca-4,8-dienal | Floral, spicy, green, citrus, muguet, ozonic, metallic and rubbery |
| Mixture of Structure 7, 8, 9 and 10 | 5-Ethyl-9-methyl-decanal, 4-ethyl-2,8-dimethyl-nonanal, 6,10-dimethyl-undecanal and 2,5,9-trimethyl-decanal | Strong woody, spicy, citrus and sweet |
| Mixture of Structure 13 and 14 | 5-Methyl-hept-5-enal and 2,4-dimethyl-hex-4-enal | Green, ozonic, metallic, rubbery and fishy |
| Mixture of Structure 15 and 16 | 5-Methyl-heptanal and 2,4-dimethy-hexanal | Floral, green, fruity, ozonic and solventy |
| Mixture of Structure 18 and 19 | 4,6-Dimethyl-hept-5-enal and 2,3,5-trimethyl-hex-4-enal | Floral, green, vegetal and chemical |
| Mixture of Structure 20 and 21 | 4,6-Dimethyl-heptanal and 2,3,5-trimethyl-hexanal | Floral, spicy, green and solventy |
| Mixture of Structure 23 and 24 | Hept-5-enal and 2-methyl-hex-4-enal | Floral, green, gassy and oily |
| Mixture of Structure 27 and 28 | 4-Methyl-hept-5-enal and 2,3-dimethyl-hex-4-enal | Green, fruity, ozonic, fatty and chemical |
| Mixture of Structure 29 and 30 | 4-Methyl-heptanal and 2,3-dimethyl-hexanal | Green, chemical, fatty and rubbery |

Example XXIII (Continued)

| Structure No. | Compound | Odor Profile |
|---|---|---|
| Mixture of Structure 33 and 34 | 3,6-Dimethyl-hept-5-enal and 3,5-dimethyl-hept-5-enal | Woody, floral, green, citrus, fruity, ozonic and plastic |
| Mixture of Structure 35 and 36 | 3,6-Dimethyl-heptanal and 3,5-dimethyl-heptanal | Floral, spicy, green, citrus and sweaty |
| Mixture of Structure 38, 39 and 40 | 3-Methyl-hept-5-enal, 2,5-dimethyl-hex-5-enal and 2-ethyl-4-methyl-pent-4-enal | Spicy, aldehydic, green, woody and cuminic |
| Structure 42 | 2,4,6-Trimethyl-hept-5-enal | Floral, aldehydic, green and weak |
| Structure 43 | Decanal | Citrus, crispy, clean and simple |
| Structure 44 | Dodecanal | Strong and chemical |
| Structure 45 | Tetradecanal | Strong, chemical and fatty |
| Structure 46 | 5,9-Dimethyl-decanal | Spicy, aldehydic, weak and simple |

Structure 7, 8, 9 and 10 exhibited particularly desirable, strong, and complex odors with no off-notes, superior to all other structures. Its advantageous properties are unexpected.

Example XXIV

Establishment of Malodor Models:

The sweat, mold/mildew, bathroom and smoke malodor models were prepared based on Applicants' proprietary formulations for assessing the effectiveness of various malodor counteractants.

Preparation of Test Samples:

Two aluminum dishes were placed in an 8 oz glass jar. A malodor material was pipetted into one aluminum dish, and an aldehyde compound prepared above (EXAMPLE I-XXI) diluted in a solvent (1%) or a solvent alone control was pipetted into the other aluminum dish. The jar was then capped and the samples were allowed to equilibrate for one hour before the testing.

Testing Procedure:

Test samples were presented in a blind and random order to 15-18 internal panelists (consisting of men/women with an age range of 25 to 55). However, different odor samples were arranged in an alternative order (for example, sweat, mold/mildew, sweat, mold/mildew, and etc.).

The panelists were instructed to take the steps of i) sniff jars containing only the malodor materials for familiarization prior to the testing; ii) uncap a jar; iii) place their noses at a distance of about 3-4 inches above the opening; iv) take short sniffs for 3 seconds; and v) enter a rating of overall intensity and malodor intensity on a handheld computer.

The overall and malodor intensity was rated using the Labeled Magnitude Scale (LMS) [Green, et al., Chemical Senses, 21(3), June 1996, 323-334]. Percent malodor reduction ("% MOR") represents the perceived reduction in mean malodor intensity of the sample containing the malodor in the presence of a malodor counteractant relative to the negative control (Malodor Alone).

Results and Discussion:

The mean ranks of the malodor coverage for the above test were as follows:

| Structure No. | Malodor | % MOR |
|---|---|---|
| Mixture of Structure 3, 4, 5 and 6 | Sweat | 57.94 |
| | Mold/Mildew | 57.34 |
| | Bathroom | 70.59 |
| | Smoke | 52.64 |
| Mixture of Structure 7, 8, 9 and 10 | Sweat | 69.07 |
| | Mold/Mildew | 70.35 |
| | Bathroom | 73.77 |
| | Smoke | 69.64 |
| Mixture of Structure 13 and 14 | Sweat | 93.96 |
| | Mold/Mildew | 94.08 |
| | Bathroom | 91.97 |
| | Smoke | 91.34 |
| Mixture of Structure 18 and 19 | Sweat | 88.11 |
| | Mold/Mildew | 72.30 |
| | Bathroom | 86.08 |
| | Smoke | 72.64 |
| Mixture of Structure 33 and 34 | Sweat | 94.60 |
| | Mold/Mildew | 85.70 |
| | Bathroom | 92.79 |
| | Smoke | 90.20 |
| Mixture of Structure 35 and 36 | Sweat | 89.04 |
| | Mold/Mildew | 78.46 |
| | Bathroom | 91.05 |
| | Smoke | 83.27 |
| Structure 42 | Sweat | 64.41 |
| | Mold/Mildew | 59.44 |
| | Bathroom | 51.19 |
| | Smoke | 55.74 |

The above aldehyde compounds including Structure 7, 8, 9 and 10 were demonstrated effective in counteracting various types of malodors.

What is claimed is:

1. A method of improving, enhancing or modifying a fragrance formulation comprising adding an olfactory acceptable amount of a mixture of 5-ethyl-9-methyl-decanal, 4-ethyl-2,8-dimethyl-nonanal, 6,10-dimethyl-undecanal, and 2,5,9-trimethyl-decanal to said formulation.

2. The method of claim 1, wherein the olfactory acceptable amount is from about 0.005 to about 50 weight percent of the fragrance formulation.

3. The method of claim 2, wherein the olfactory acceptable amount is from about 0.1 to about 25 weight percent of the fragrance formulation.

4. The method of claim 2, wherein the olfactory acceptable amount is from about 0.5 to about 10 weight percent of the fragrance formulation.

* * * * *